United States Patent
Aida

(10) Patent No.: US 9,550,717 B2
(45) Date of Patent: Jan. 24, 2017

(54) METHOD FOR RECOVERING ANIONIC FLUORINATED EMULSIFIER

(71) Applicant: ASAHI GLASS COMPANY, LIMITED, Tokyo (JP)

(72) Inventor: Shigeru Aida, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 14/794,069

(22) Filed: Jul. 8, 2015

(65) Prior Publication Data
US 2015/0307434 A1 Oct. 29, 2015

Related U.S. Application Data

(63) Continuation of application No. PCT/JP2014/055148, filed on Feb. 28, 2014.

(30) Foreign Application Priority Data

Mar. 6, 2013 (JP) ................................ 2013-043967

(51) Int. Cl.
| | | |
|---|---|---|
| C07C 51/487 | (2006.01) |
| B01J 41/04 | (2006.01) |
| B01J 49/00 | (2006.01) |
| C07C 59/135 | (2006.01) |
| B01D 15/20 | (2006.01) |
| B01D 15/36 | (2006.01) |

(52) U.S. Cl.
CPC ........... *C07C 51/487* (2013.01); *B01D 15/203* (2013.01); *B01D 15/363* (2013.01); *B01J 41/04* (2013.01); *B01J 49/00* (2013.01); *C07C 59/135* (2013.01)

(58) Field of Classification Search
CPC ... C07C 51/487; C07C 59/135; B01D 15/363; B01D 15/203; B01J 41/04; B01J 49/00
See application file for complete search history.

(56) References Cited

U.S. PATENT DOCUMENTS

| 4,282,162 A | 8/1981 | Kuhls |
|---|---|---|
| 8,492,585 B2 | 7/2013 | Haga et al. |
| 9,045,411 B2 | 6/2015 | Aida et al. |
| 2004/0010156 A1 | 1/2004 | Kondo et al. |
| 2012/0271065 A1 | 10/2012 | Haga et al. |

FOREIGN PATENT DOCUMENTS

| JP | 63-2656 | 1/1988 |
|---|---|---|
| JP | 2002-59160 | 2/2002 |
| WO | WO 2011/096448 | 8/2011 |

OTHER PUBLICATIONS

International Search Report issued Apr. 22, 2014, in PCT/JP2014/055148 filed Feb. 28, 2014.

*Primary Examiner* — Shailendra Kumar

(74) *Attorney, Agent, or Firm* — Oblon, McClelland, Maier & Neustadt, L.L.P.

(57) ABSTRACT

A method for recovering an anionic fluorinated emulsifier comprises contacting a strongly basic ion exchange resin having an anionic fluorinated emulsifier adsorbed thereon to an aqueous inorganic acid solution and an organic solvent comprising a nitrile group. The anionic fluorinated emulsifier is eluted from the strongly basic ion exchange resin, and a liquid phase comprising an acid of the anionic fluorinated emulsifier is obtained. An acid of the anionic fluorinated emulsifier is recovered from the liquid phase. The strongly basic ion exchange resin and the liquid phase are preferably separated, after the aqueous inorganic acid solution and the organic solvent are contacted to the strongly basic ion exchange resin, and before the acid of the anionic fluorinated emulsifier is recovered from the liquid phase.

13 Claims, No Drawings

METHOD FOR RECOVERING ANIONIC FLUORINATED EMULSIFIER

This application is a CON of PCT/JP2014/055148, filed on Feb. 28, 2014.

TECHNICAL FIELD

The present invention relates to a method for recovering an anionic fluorinated emulsifier, which comprises eluting an anionic fluorinated emulsifier from a basic ion exchange resin having the anionic fluorinated emulsifier adsorbed thereon and recovering it as an acid of the anionic fluorinated emulsifier.

BACKGROUND ART

At the time of producing a fluorinated polymer such as a polytetrafluoroethylene (hereinafter referred to as PTFE), a melt-processable fluororesin or a fluoroelastomer by emulsion polymerization, it is common to use an anionic fluorinated emulsifier in order not to hinder the polymerization reaction by chain transfer in an aqueous medium.

An aqueous emulsion of a fluorinated polymer (hereinafter referred to as a fluorinated polymer aqueous emulsion) obtained by emulsion polymerization is subjected to coagulation, followed by drying, to obtain a powder of the fluorinated polymer. A powder of a fluorinated polymer, particularly a fine powder of PTFE, is molded by a method such as paste extrusion molding and then, used for various applications. Otherwise, if necessary, a nonionic surfactant, etc. may be added to a fluorinated polymer aqueous emulsion for stabilization treatment, followed by concentration treatment to obtain a fluorinated polymer aqueous dispersion containing the fluorinated polymer at a high concentration. Such a fluorinated polymer aqueous dispersion may be used, if necessary, by an addition of various compounding ingredients, for various coating applications, impregnation applications, etc.

On the other hand, an anionic fluorinated emulsifier to be used for emulsion polymerization of a fluorinated polymer is not easily decomposed in the natural world. Therefore, in recent years, it is desired to reduce an anionic fluorinated emulsifier contained not only in industrial effluents but also in products such as a fluorinated polymer aqueous emulsion, a fluorinated polymer aqueous dispersion, etc.

As a method for reducing an anionic fluorinated emulsifier, there is a method wherein a liquid to be treated, such as an aqueous emulsion or an aqueous dispersion, containing an anionic fluorinated emulsifier, is contacted to a basic ion exchange resin, so that the anionic fluorinated emulsifier in the liquid to be treated is adsorbed on the basic ion exchange resin. Further, since the anionic fluorinated emulsifier is expensive, it has been attempted to recover and reuse the anionic fluorinated emulsifier adsorbed on the basic ion exchange resin.

For example, Patent Document 1 discloses a method of treating a basic ion exchange resin having an anionic fluorinated emulsifier adsorbed thereon, with a mixture of a dilute mineral acid and an organic solvent, to recover the emulsifier as an acid of the anionic fluorinated emulsifier. It is disclosed that the organic solvent is preferably a solvent which is miscible with water to present a solubility of at least 40% or which can be unlimitedly mixed with water, and an alcohol such as methanol, a cyclic ether such as dioxane, methylene chloride, etc. may be used.

Further, Patent Document 2 discloses a method wherein by means of an inorganic acid and a water-insoluble fluorinated medium, from a basic ion exchange resin having an anionic fluorinated emulsifier adsorbed thereon, an acid of the anionic fluorinated emulsifier is eluted in the water-insoluble fluorinated medium for recovery.

PRIOR ART DOCUMENTS

Patent Documents

Patent Document 1: JP-B-63-2656
Patent Document 2: WO/2011/096448

DISCLOSURE OF INVENTION

Technical Problem

In Examples of Patent Document 1, an anionic fluorinated emulsifier is recovered in a good yield of at least 80% from a weakly basic ion exchange resin, by using, as an organic solvent, an alcohol such as methanol or a cyclic ether such as dioxane.

However, in the case of eluting and recovering the emulsifier by using methanol from a strongly basic ion exchange resin having a high ability to adsorb the anionic fluorinated emulsifier, the recovery rate of the anionic fluorinated emulsifier was low at a level of 70%. Further, depending upon the type of the anionic fluorinated emulsifier, the emulsifier was likely to react with methanol to form an ester, and it was difficult to convert it to an ammonium salt or the like useful as an emulsifier.

Further, in Patent Document 2, an anionic fluorinated emulsifier was recovered from a basic ion exchange resin having the anionic fluorinated emulsifier adsorbed thereon by using a water-insoluble fluorinated medium as a non-flammable organic solvent, but the recovery rate of the anionic fluorinated emulsifier recovered by a single extraction operation was as low as 50%.

Accordingly, it is an object of the present invention to provide a method for recovering an anionic fluorinated emulsifier, whereby the anionic fluorinated emulsifier adsorbed on a basic ion exchange resin can be simply and efficiently recovered.

Solution to Problem

The present invention provides a method for recovering an anionic fluorinated emulsifier, having the following constructions [1] to [13].

[1] A method for recovering an anionic fluorinated emulsifier, which comprises eluting an anionic fluorinated emulsifier from a basic ion exchange resin having the anionic fluorinated emulsifier adsorbed thereon and recovering it as an acid of the anionic fluorinated emulsifier, and which is characterized by using an aqueous inorganic acid solution and an organic solvent having a nitrile group to recover, from the basic ion exchange resin, the acid of the anionic fluorinated emulsifier.

[2] The method for recovering an anionic fluorinated emulsifier according to the above [1], which comprises eluting an anionic fluorinated emulsifier from a basic ion exchange resin having the anionic fluorinated emulsifier adsorbed thereon and recovering it as an acid of the anionic fluorinated emulsifier, wherein after the aqueous inorganic acid solution and the organic solvent having a nitrile group are contacted to the basic ion exchange resin, the basic ion exchange resin and a liquid phase are separated to recover the liquid phase, and from the liquid phase, the acid of the anionic fluorinated emulsifier is recovered.

[3] The method for recovering an anionic fluorinated emulsifier according to the above [1], which comprises eluting an anionic fluorinated emulsifier from a basic ion exchange resin having the anionic fluorinated emulsifier adsorbed thereon and recovering it as an acid of the anionic fluorinated emulsifier, wherein to the basic ion exchange resin, the aqueous inorganic acid solution is contacted and then the organic solvent having a nitrile group is contacted, thereafter the basic ion exchange resin and a liquid phase are separated to recover the liquid phase, and from the liquid phase, the acid of the anionic fluorinated emulsifier is recovered.

[4] The method for recovering an anionic fluorinated emulsifier according to the above [3], wherein after contacting the aqueous inorganic acid solution to the basic ion exchange resin, the basic ion exchange resin is separated and recovered, and to the separated and recovered basic ion exchange resin, the organic solvent having a nitrile group is contacted.

[5] The method for recovering an anionic fluorinated emulsifier according to any one of the above [1] to [4], wherein the aqueous inorganic acid solution is at least one member selected from the group consisting of an aqueous hydrochloric acid solution, an aqueous sulfuric acid solution, an aqueous nitric acid solution and an aqueous phosphoric acid solution.

[6] The method for recovering an anionic fluorinated emulsifier according to any one of the above [1] to [5], wherein the organic solvent having a nitrile group is at least one member selected from the group consisting of acetonitrile, propionitrile, butyronitrile and isobutyronitrile.

[7] The method for recovering an anionic fluorinated emulsifier according to any one of the above [1] to [6], wherein the acid of the anionic fluorinated emulsifier is a fluorinated carboxylic acid.

[8] The method for recovering an anionic fluorinated emulsifier according to the above [7], wherein the acid of the anionic fluorinated emulsifier is a $C_{5-7}$ fluorinated carboxylic acid which may have from 1 to 3 etheric oxygen atoms.

[9] The method for recovering an anionic fluorinated emulsifier according to any one of the above [1] to [8], wherein the basic ion exchange resin is a strongly basic ion exchange resin.

[10] The method for recovering an anionic fluorinated emulsifier according to any one of the above [1] to [9], wherein the concentration of the aqueous inorganic acid solution is at least 5.0 mass %.

[11] The method for recovering an anionic fluorinated emulsifier according to any one of the above [1] to [10], wherein the aqueous inorganic acid solution is used within such a range that the acid of the anionic fluorinated emulsifier to be eluted/the inorganic acid is from 1/20 to 1.5/1 by molar ratio.

[12] The method for recovering an anionic fluorinated emulsifier according to any one of the above [1] to [11], wherein the ratio of the basic ion exchange resin to the aqueous inorganic acid solution is from 90/10 to 10/90 by mass ratio.

[13] The method for recovering an anionic fluorinated emulsifier according to any one of the above [1] to [12], wherein the ratio of the basic ion exchange resin to the organic solvent having a nitrile group is from 10/90 to 70/30 by mass ratio.

Advantageous Effects of Invention

According to the present invention, to a basic ion exchange resin having an anionic fluorinated emulsifier adsorbed thereon, an aqueous inorganic acid solution and an organic solvent having a nitrile group are contacted, or to such a basic ion exchange resin, an aqueous inorganic acid solution is contacted, and then, an organic solvent having a nitrile group is contacted thereto, whereby the anionic fluorinated emulsifier adsorbed on the basic ion exchange resin is converted to an acid-form by the aqueous inorganic acid solution and eluted in the organic solvent having a nitrile group. And, in the present invention, an organic solvent having a nitrile group is used for extraction, whereby the anionic fluorinated emulsifier can be recovered in good yield. Further, unlike an alcohol, the organic solvent having a nitrile group does not react with the anionic fluorinated emulsifier, and thus after the organic solvent having a nitrile group is separated, the recovered acid of the anionic fluorinated emulsifier may be used, as it is, for emulsion polymerization for a fluorinated polymer, or may be neutralized and used as e.g. an ammonium salt or an alkali metal salt.

DESCRIPTION OF EMBODIMENTS

In the present invention, the anionic fluorinated emulsifier to be adsorbed on a basic ion exchange resin is not particularly limited. For example, it may be a fluorinated carboxylic acid which may have an etheric oxygen atom or its salt, or a fluorinated sulfonic acid or its salt. The salt may, for example, be an ammonium salt or an alkali metal salt (such as Li, Na or K), preferably an ammonium salt. Among them, a fluorinated carboxylic acid which may have an etheric oxygen atom, or its salt, is preferred, and a $C_{5-7}$ fluorinated carboxylic acid which may have from 1 to 3 etheric oxygen atoms, or its salt, is more preferred. A $C_{5-7}$ fluorinated carboxylic acid which may have from 1 to 3 etheric oxygen atoms, or its salt, is most preferred.

Specific examples of the fluorinated carboxylic acid include, a perfluorocarboxylic acid, a perfluorocarboxylic acid having an etheric oxygen atom, a fluorinated carboxylic acid having a hydrogen atom, etc.

The perfluorocarboxylic acid includes, for example, perfluorohexanoic acid, perfluoroheptanoic acid, perfluorooctanoic acid, perfluorononanoic acid, etc.

The perfluorocarboxylic acid having an etheric oxygen atom includes, for example, $C_3F_7OCF(CF_3)CF_2OCF(CF_3)$ COOH, $C_4F_9OC_2F_4OCF_2COOH$, $C_3F_7OC_2F_4OCF_2COOH$, $C_2F_5OC_2F_4OCF_2COOH$, $C_2F_5OCF_2CF_2OCF_2CF_2OCF_2COOH$, $C_2F_5O(CF_2)_5COOH$, $CF_3OC_2F_4OCF_2COOH$, $CF_3OCF_2OCF_2OCF_2COOH$, $CF_3OCF_2OCF_2OCF_2OCF_2COOH$, $CF_3O(CF_2CF_2O)_2CF_2COOH$, $CF_3OCF_2CF_2CF_2OCF_2COOH$, $CF_3OCF_2CF_2CF_2OCF_2CF_2COOH$, $C_4F_9OCF_2COOH$, $C_4F_9OCF_2CF_2COOH$, $CF_3OCF(CF_3)CF_2OCF(CF_3)COOH$, $C_4F_9OCF(CF_3)COOH$, $C_3F_7OCF(CF_3)COOH$, etc.

The fluorinated carboxylic acid having a hydrogen atom includes, for example, ω-hydroperfluorooctanoic acid, $C_3F_7OCF(CF_3)CF_2OCHFCOOH$, $CF_3CFHO(CF_2)_5COOH$, $CF_3O(CF_2)_3OCHFCF_2COOH$, $CF_3O(CF_2)_3OCHFCOOH$, $C_3F_7OCHFCF_2COOH$, $CF_3CFHO(CF_2)_3COOH$, etc.

The fluorinated sulfonic acid includes, for example, perfluorooctane sulfonic acid, $C_6F_{13}CH_2CH_2SO_3H$, etc.

In the present invention, the basic ion exchange resin to be used for adsorbing the anionic fluorinated emulsifier may be a strongly basic ion exchange resin or a weakly basic ion exchange resin, preferably a strongly basic ion exchange resin. The strongly basic ion exchange resin is less susceptible to an influence by the pH of the liquid to be treated containing the anionic fluorinated emulsifier and thus can maintain high adsorbing efficiency. Further, the strongly basic ion exchange resin adsorbs the anionic fluorinated emulsifier firmly so that the anionic fluorinated emulsifier tends to be hardly eluted from the strongly basic ion exchange resin, whereby the recovery rate of the anionic fluorinated emulsifier tends to be low. However, by the method of the present invention, even in a case where the anionic fluorinated emulsifier is adsorbed on the strongly basic ion exchange resin, the anionic fluorinated emulsifier can be recovered in good yield.

The strongly basic ion exchange resin may be one having a quaternary ammonium group such as a trimethylammonium group or a dimethylethanolammonium group introduced as an ion exchange group to a resin matrix.

The weakly basic ion exchange resin may be one having a primary to tertiary amino group such as a dimethylammonium group or an amino group introduced as an ion exchange group to a resin matrix.

The material for the resin matrix of the basic ion exchange resin is not particularly limited. A styrene/divinyl benzene cross-linked resin, an acryl/divinyl benzene cross-linked resin or a cellulose resin may, for example, be mentioned.

The type of the basic ion exchange resin is not particularly limited, and either porous type or gel type may be preferably used.

The average particle size of the basic ion exchange resin is preferably from 0.1 to 5 mm, more preferably from 0.2 to 2 mm, particularly preferably from 0.3 to 1.5 mm. When the average particle size of the basic ion exchange resin is within the above range, for example, the flow path of the liquid to be treated is less likely to be clogged, when the liquid to be treated containing the anionic fluorinated emulsifier is permitted to flow through a column packed with the basic ion exchange resin to carry out the operation to let the anionic fluorinated emulsifier be adsorbed.

The ion exchange capacity of the basic ion exchange resin is preferably from 0.1 to 3 (eq/L), more preferably from 0.5 to 2.5 (eq/L). When the ion exchange capacity of the basic ion exchange resin is within the above range, the anionic fluorinated emulsifier in the liquid to be treated can efficiently be adsorbed.

Commercial products of the basic ion exchange resin include, for example, Lewatit (registered trademark) MP800OH manufactured by Lanxess, Lewatit (registered trademark) M800KR manufactured by Lanxess, Lewatit (registered trademark) MP600 manufactured by Lanxess, Lewatit (registered trademark) MP62WS manufactured by Lanxess, PUROLITE (registered trademark) A200MBOH manufactured by Purolite K.K., PUROLITE (registered trademark) A300MBOH manufactured by Purolite K.K., PUROLITE (registered trademark) A503OH manufactured by Purolite K.K., etc.

In the present invention, the basic ion exchange resin having an anionic fluorinated emulsifier adsorbed thereon, is obtainable by contacting a liquid to be treated containing an anionic fluorinated emulsifier to a basic ion exchange resin. That is, by contacting the liquid to be treated, to a basic ion exchange resin, the anionic fluorinated emulsifier in the liquid to be treated, is adsorbed on the basic ion exchange resin. For example, in a case where a liquid to be treated containing $CF_3CF_2OCF_2CF_2OCF_2COO^-$ $(NH4)^+$ as an anionic fluorinated emulsifier is contacted with a basic ion exchange resin, $CF_3CF_2OCF_2CF_2OCF_2COO^-$ is considered to be bonded to and adsorbed on an ion exchange group of the basic ion exchange resin.

As the liquid to be treated containing an anionic fluorinated emulsifier, the following (1) to (3) may, for example, be mentioned.

(1) A fluorinated polymer aqueous dispersion obtained by subjecting a fluorinated monomer to emulsion polymerization in the presence of an anionic fluorinated emulsifier, and adding a nonionic surfactant to the obtained fluorinated polymer aqueous emulsion for stabilization, if required, followed by concentration.

(2) Waste water containing an anionic fluorinated emulsifier discharged after coagulating the above fluorinated polymer aqueous emulsion.

(3) An aqueous solution having absorbed an anionic fluorinated emulsifier discharged in the atmosphere in the process for drying a fluorinated polymer coagulate obtained by coagulating the above fluorinated polymer aqueous emulsion.

The above fluorinated polymer dispersion is preferably a fluorinated polymer aqueous dispersion obtained by stabilizing the fluorinated polymer aqueous emulsion by a nonionic surfactant.

The nonionic surfactant may, for example, be a surfactant represented by the following formula (A) or (B).

$$R^1\text{---}O\text{-}A\text{-}H \quad (A)$$

In the formula (A), $R^1$ is a $C_{8\text{-}18}$ alkyl group, and A is a polyoxyalkylene chain constituted by from 5 to 20 oxyethylene groups and from 0 to 2 oxypropylene groups.

$$R^2\text{---}C_6H_4\text{---}O\text{---}B\text{---}H \quad (B)$$

In the formula (B), $R^2$ is a $C_{4\text{-}12}$ alkyl group, and B is a polyoxyethylene chain constituted by from 5 to 20 oxyethylene groups.

Specific examples of the nonionic surfactant of the formula (A) include nonionic surfactants having molecular structures of $C_{13}H_{27}\text{---}(OC_2H_4)_{10}\text{---}OH$, $C_{12}H_{25}\text{---}(OC_2H_4)_{10}\text{---}OH$, $C_{10}H_{21}CH(CH_3)CH_2\text{---}(OC_2H_4)_9\text{---}OH$, $C_{13}H_{27}\text{---}(OC_2H_4)_8\text{---}OCH(CH_3)CH_2\text{---}OH$, $C_{16}H_{33}\text{---}(OC_{21}H_4)_{10}\text{---}OH$, $CH(C_5H_{11})(C_7H_{15})\text{---}(OC_2H_4)_9\text{---}OH$, etc. Commercial products include TERGITOL (registered trademark) 15S series, manufactured by The Dow Chemical Company, Newcol (registered trademark) series, manufactured by Nippon Nyukazai Co., Ltd., Lionol (registered trademark) TD series, manufactured by Lion Corporation, etc.

Specific examples of the nonionic surfactant of the formula (B) include, for example, nonionic surfactants having molecular structures of $C_8H_{17}\text{---}C_6H_4\text{---}(OC_2H_4)_{10}\text{---}OH$, $C_9H_{19}\text{---}C_6H_4\text{---}(OC_2H_4)_{10}\text{---}OH$, etc. Commercial products include Triton (registered trademark) X series, manufactured by The Dow Chemical Company, Nikkol (registered trademark) OP series or NP series, manufactured by Nikko Chemicals Co., Ltd., etc.

The content of a nonionic surfactant represented by the formula (A) and/or (B) in the fluorinated polymer aqueous dispersion is preferably from 1 to 20 mass %, more preferably from 1 to 10 mass %, particularly preferably from 2 to 8 mass %, based on the mass of the fluorinated polymer.

The method for contacting the liquid to be treated containing an anionic fluorinated emulsifier and the basic ion exchange resin is not particularly limited, and a conventional method may be mentioned. For example, it may be a method of putting the basic ion exchange resin into the liquid to be treated, followed by stirring or vibrating, or a method of passing the liquid to be treated, through a column packed with the basic ion exchange resin. Further, prior to contacting the liquid to be treated, to the basic ion exchange resin, the liquid to be treated may preferably be subjected to filtration to remove any floating solid, etc. such as coagulation, whereby it is possible to prevent e.g. clogging of the basic ion exchange resin. Such filtration of the liquid to be treated, is preferably conducted by means of a single stage or multistage filters having pore sizes of from 0.1 to 300 μm, preferably from 1 to 100 μm.

The contact temperature at the time of contacting the liquid to be treated containing an anionic fluorinated emulsifier to the basic ion exchange resin is not particularly limited. It may suitably be selected but is preferably in the vicinity of room temperature of from 10 to 40° C. Further, the contact time is not particularly limited and may suitably be selected. For example, in the case of contacting by a stirring system, it is preferably within a range of from 10 minutes to 200 hours, more preferably within a range of from 30 minutes to 50 hours. Further, the pressure at the time of contact is preferably the atmospheric pressure, but it may be under a reduced pressure condition or an elevated pressure condition.

As mentioned above, by letting an anionic fluorinated emulsifier in the liquid to be treated, be adsorbed on a basic ion exchange resin, followed by separating the basic ion exchange resin, it is possible to obtain the basic ion exchange resin having the anionic fluorinated emulsifier adsorbed thereon. Such a basic ion exchange resin having the anionic fluorinated emulsifier adsorbed thereon may be used in a wet state without conducting drying treatment, etc. or may be subjected to drying treatment and used in a dried state. Industrially, it is preferred to use it as it is in a wet state, whereby the process can be simplified.

In the present invention, in the method for recovering an anionic fluorinated emulsifier, by using an aqueous inorganic acid solution and an organic solvent having a nitrile group, from the basic ion exchange resin, an acid of the anionic fluorinated emulsifier is recovered.

In a first embodiment of the method for recovering an anionic fluorinated emulsifier in the present invention, firstly an aqueous inorganic acid solution and an organic solvent having a nitrile group are contacted to the basic ion exchange resin having an anionic fluorinated emulsifier adsorbed thereon.

When an elution extraction medium is contacted to a basic ion exchange resin having an anionic fluorinated emulsifier adsorbed thereon, the anionic fluorinated emulsifier is converted to an acid-form by the aqueous inorganic acid solution and thus tends to be easily eluted from the basic ion exchange resin. The anionic fluorinated emulsifier has good compatibility with the organic solvent having a nitrile group, and therefore, the anionic fluorinated emulsifier adsorbed on the basic ion exchange resin is eluted as an acid of the anionic fluorinated emulsifier and extracted in the organic solvent having a nitrile group. And, in the present invention, by use of the organic solvent having a nitrile group which has high compatibility with the acid of the anionic fluorinated emulsifier for extraction, it is possible to efficiently extract the acid of the anionic fluorinated emulsifier. Further, unlike the alcohol, the organic solvent having a nitrile group does not react with the acid of the anionic fluorinated emulsifier, and thus after the organic solvent having a nitrile group is separated, the extracted acid of the anionic fluorinated emulsifier may be used as it is, or as e.g. an ammonium salt or an alkali metal salt after neutralized.

The ratio of the basic ion exchange resin to the aqueous inorganic acid solution and the organic solvent having a nitrile group (hereinafter they will sometimes be referred to as elution extraction medium) is such that the basic ion exchange resin/the elution extraction medium is preferably from 1/99 to 99/1, more preferably from 10/90 to 90/10, most preferably from 15/85 to 50/50, by mass ratio. When the ratio of the basic ion exchange resin to the elution extraction medium is within the above range, it is possible to efficiently contact the basic ion exchange resin and the elution extraction medium.

The contact time of the basic ion exchange resin and the elution extraction medium is preferably from 5 to 500 minutes, more preferably from 10 to 300 minutes. When the contact time is at least 5 minutes, it is possible to sufficiently extract the acid of the anionic fluorinated emulsifier. Even if the contact time exceeds 500 minutes, there is no substantial change in the amount of extraction of the acid of the anionic fluorinated emulsifier, and therefore, the upper limit is preferably 500 minutes. The temperature at the time of contacting the elution extraction medium is preferably from 5 to 100° C., more preferably from 10 to 80° C. When it is at least 5° C., it is possible to efficiently extract the acid of the anionic fluorinated emulsifier. When it is at most 100° C., the organic solvent having a nitrile group and the acid of the anionic fluorinated emulsifier will not be decomposed, and therefore, the upper limit is preferably 100° C.

The method for contacting the basic ion exchange resin and the elution extraction medium is not particularly limited. For example, a method of putting the basic ion exchange resin and the elution extraction medium in an autoclave, followed by mechanical stirring by stirring vanes, or a method of contacting the basic ion exchange resin and the elution extraction medium by means of a shaking machine, may be mentioned. Otherwise, the basic ion exchange resin may be packed in a column, and the elution extraction medium is permitted to flow therethrough, so that the acid of the anionic fluorinated emulsifier may be extracted in the elution extraction medium by a flow-through extraction method.

As the aqueous inorganic acid solution, at least one member selected from the group consisting of an aqueous hydrochloric acid solution, an aqueous sulfuric acid solution, an aqueous nitric acid solution and an aqueous phosphoric acid solution, is preferably used. Two or more types of such aqueous inorganic acid solutions may be used in combination. Among them, an aqueous hydrochloric acid solution is particularly preferred, since its use is industrially simple.

The concentration of the aqueous inorganic acid solution is usually preferably high, since as it becomes high, the acid of the anionic fluorinated emulsifier to be eluted from the basic ion exchange resin tends to increase. It is preferably at least 1.0 mass %, more preferably at least 5.0 mass %, particularly preferably from 10 to 38 mass %.

The amount of the inorganic acid to be used is such that the acid of the anionic fluorinated emulsifier to be eluted/the inorganic acid is preferably from 1/30 to 1/1, more preferably from 1/20 to 1.5/1, most preferably from 1/15 to 2/1 by molar ratio.

The organic solvent having a nitrile group may, for example, be acetonitrile, propionitrile, butyronitrile, isobutyronitrile and benzonitrile. Preferred is at least one member selected from the group consisting of acetonitrile, propionitrile, butyronitrile and isobutyronitrile. Further, since the basic ion exchange resin contains water, acetonitrile or propionitrile having high compatibility with water is more preferred, and acetonitrile is most preferred. When the organic solvent having a nitrile group is water-soluble, the penetrability of the elution extraction medium to the basic ion exchange resin will be better, whereby it becomes easy to extract the anionic fluorinated emulsifier from the basic ion exchange resin.

The solubility in water at 20° C. of the organic solvent having a nitrile group is preferably at least 5%, more preferably at least 10%, most preferably at least 50%.

The organic solvent having a nitrile group is preferably readily separated by distillation from the acid of the anionic fluorinated emulsifier. If the medium to extract the acid of the anionic fluorinated emulsifier forms an azeotropic mixture with the acid of the emulsifier, it is difficult to purify the acid of the anionic fluorinated emulsifier. For example, $CF_3CF_2OCF_2CF_2OCF_2COOH$ and acetonitrile do not form an azeotropic mixture, whereby the acid of the anionic fluorinated emulsifier will readily be purified by distillation.

In the elution extraction medium, the ratio of the aqueous inorganic acid solution to the organic solvent having a nitrile group is preferably the aqueous inorganic acid solution/the organic solvent having a nitrile group is from 1/99 to 95/5, more preferably from 5/95 to 80/20, particularly preferably from 10/90 to 70/30, by mass ratio. When the mass ratio of the aqueous inorganic acid solution to the organic solvent having a nitrile group is within the above range, the recovery rate of the acid of the anionic fluorinated emulsifier is high.

In the above embodiment, from the mixture of the basic ion exchange resin and the elution extraction medium, the basic ion exchange resin is separated and removed, and a liquid phase is separated and recovered, and from the recovered liquid phase, the acid of the anionic fluorinated emulsifier is recovered. In a case where the recovered liquid phase is a single phase, that is, in a case where the aqueous inorganic acid solution and the organic solvent having a nitrile group constitute a uniform phase, by carrying out e.g. a distillation operation of the recovered liquid phase, the acid of the anionic fluorinated emulsifier can be recovered.

The acid of the anionic fluorinated emulsifier contained in the recovered liquid phase can be quantitatively analyzed by e.g. an analytical method disclosed in JIS Water quality K0400-30-10, an analytical method by gas chromatography, or an NMR analytical method using $^1$H-NMR and $^{19}$F-NMR.

The acid of the anionic fluorinated emulsifier thus recovered is separated from the organic solvent having a nitrile group via a purification step such as distillation, and may be used as it is as an anionic fluorinated emulsifier, or may be neutralized and used as an ammonium salt, an alkali metal salt or the like.

Now, a second embodiment of the method for recovering an anionic fluorinated emulsifier in the present invention will be described.

In the second embodiment, an aqueous inorganic acid solution is contacted to a basic ion exchange resin having an anionic fluorinated emulsifier adsorbed thereon, and then, an organic solvent having a nitrile group is contacted thereto.

As mentioned above, when an aqueous inorganic acid solution is contacted to the basic ion exchange resin, the anionic fluorinated emulsifier is converted to an acid-form and adsorbed on the basic ion exchange resin in a form to be readily eluted. The anionic fluorinated emulsifier has low compatibility with the aqueous inorganic acid solution, whereby even if converted to an acid-form, it will scarcely be eluted in the aqueous inorganic acid solution. However, the anionic fluorinated emulsifier has good compatibility with the organic solvent having a nitrile group, and when the organic solvent having a nitrile group is contacted to the basic ion exchange resin contacted with the aqueous inorganic acid solution, the anionic fluorinated emulsifier adsorbed on the basic ion exchange resin will be eluted and extracted as an acid of the anionic fluorinated emulsifier in the organic solvent having a nitrile group. Then, the basic ion exchange resin is separated and removed, and the liquid phase is recovered, and the acid of the anionic fluorinated emulsifier can be recovered by carrying out e.g. a distillation operation of the recovered liquid phase.

In the second embodiment, it is preferred that after contacting the aqueous inorganic acid solution to the basic ion exchange resin, the basic ion exchange resin is separated and recovered, and the organic solvent having a nitrile group is contacted to the separated and recovered basic ion exchange resin. Thus, it is possible to minimize the amount of the inorganic acid in contact with the organic solvent having a nitrile group so that the hydrolysis of the organic solvent having a nitrile group can be minimized.

In the second embodiment, as the aqueous inorganic acid solution and the organic solvent having a nitrile group, the same ones as described above in the first embodiment may be used.

In the second embodiment, the contact time of the basic ion exchange resin and the aqueous inorganic acid solution is preferably from 5 to 500 minutes, more preferably from 10 to 300 minutes. When the contact time is at least 5 minutes, the anionic fluorinated emulsifier can be converted to an acid-form and can be made to be readily eluted from the basic ion exchange resin. Further, even if it exceeds 500 minutes, there will be no substantial improvement in effects, and therefore, the upper limit is preferably 500 minutes.

The temperature at the time of contacting the aqueous inorganic acid solution is preferably from 5 to 100° C., more preferably from 10 to 80° C. When it is at least 5° C., the anionic fluorinated emulsifier can be converted to an acid-form and can be made to be readily eluted from the basic ion exchange resin. When it is at most 100° C., it does not exceed the boiling point under the atmospheric pressure of the aqueous inorganic acid solution, so that the treatment by the aqueous inorganic acid solution can be carried out under the atmospheric pressure, and therefore, the upper limit is preferably 100° C.

In the second embodiment, the method for contacting the basic ion exchange resin and the aqueous inorganic acid solution is not particularly limited. For example, a method of putting the basic ion exchange resin and the aqueous inorganic acid solution in an autoclave, followed by mechanical stirring by stirring vanes, or a method of contacting the basic ion exchange resin and the aqueous inorganic acid solution by means of a shaking machine, may be mentioned. Otherwise, the basic ion exchange resin may be packed in a column, and the aqueous inorganic acid solution is permitted to flow therethrough for the contact.

In the second embodiment, the ratio of the basic ion exchange resin to the aqueous inorganic acid solution is preferably from 99/1 to 1/99, more preferably from 90/10 to 10/90, most preferably from 50/50 to 30/70, by mass ratio. When the ratio of the basic ion exchange resin to the aqueous inorganic acid solution is within the above range, it is possible to efficiently contact the basic ion exchange resin and the aqueous inorganic acid solution, and the anionic fluorinated emulsifier adsorbed on the basic ion exchange resin can be made to be readily eluted.

In the second embodiment, the amount of the inorganic acid to be used is such that the acid of the anionic fluorinated emulsifier to be eluted/the inorganic acid is preferably from 1/30 to 1/1, more preferably from 1/20 to 1.5/1, most preferably from 1/15 to 2/1 by molar ratio.

In the second embodiment, the contact time of the basic ion exchange resin and the organic solvent having a nitrile group is preferably from 5 to 500 minutes, more preferably from 10 to 300 minutes. When the contact time is at least 5 minutes, it is possible to sufficiently extract the anionic fluorinated emulsifier. Even if the contact time exceeds 500 minutes, there is no substantial change in the amount of extraction of the acid of the anionic fluorinated emulsifier, and therefore, the upper limit is preferably 500 minutes.

The temperature at the time of contacting the organic solvent having a nitrile group is preferably from 5 to 100° C., more preferably from 10 to 80° C. When it is at least 5° C., it is possible to efficiently extract the acid of the anionic fluorinated emulsifier. When it is at most 100° C., the organic solvent having a nitrile group and the acid of the anionic fluorinated emulsifier will not be decomposed, and therefore, the upper limit is preferably 100° C.

In the second embodiment, the method for contacting the basic ion exchange resin and the organic solvent having a nitrile group may be carried out by the same method as the above-mentioned method for contacting the aqueous inorganic acid solution.

In the second embodiment, the ratio of the basic ion exchange resin to the organic solvent having a nitrile group is preferably from 1/99 to 80/20, more preferably from 10/90 to 70/30, most preferably from 15/85 to 60/40, by mass ratio. When the ratio of the basic ion exchange resin to the extraction medium is within the above range, it is possible to efficiently contact the basic ion exchange resin and the extraction medium and extract the acid of the anionic fluorinated emulsifier in the extraction medium.

EXAMPLES

Now, the present invention will be described in further detail with reference to Examples, but it should be understood that the present invention is by no means limited thereto.

Recovery Rate of Anionic Fluorinated Emulsifier

With respect to a liquid phase recovered after extraction treatment, the acid of the anionic fluorinated emulsifier was quantitatively analyzed by quantitative analyses by $^1$H-NMR and $^{19}$F-NMR, and the content (g) of the acid of the anionic fluorinated emulsifier in the liquid phase was measured. Then, the recovery rate of the acid of the anionic fluorinated emulsifier was obtained based on the following formula.

Recovery rate (%)=(content (g) of the acid of the anionic fluorinated emulsifier in the liquid phase/amount (g) of the anionic fluorinated emulsifier adsorbed on the basic ion exchange resin)×100

Ex. 1

An aqueous solution of an anionic fluorinated emulsifier $(CF_3CF_2OCF_2CF_2OCF_2COO^-(NH_4)^+)$ and a basic ion exchange resin (manufactured by Lanxess, Lewatit (registered trademark) MP800OH) were contacted to let the anionic fluorinated emulsifier be adsorbed on the basic ion exchange resin.

Then, into a beaker having an internal capacity of 50 ml and provided with a cover, 4.0 g of the basic ion exchange resin having the anionic fluorinated emulsifier adsorbed thereon and 4.0 g of a 18% aqueous hydrochloric acid solution were charged, and the content was stirred for 30 minutes by a magnetic stirrer while maintaining the temperature at 40° C. by a constant temperature water bath, followed by cooling to room temperature. Then, only hydrochloric acid was withdrawn from the beaker, 6.0 g of acetonitrile was charged, and the content was stirred for 30 minutes by a magnetic stirrer while maintaining the temperature at 40° C. by a constant temperature water bath, followed by cooling to room temperature. Then, the ion exchange resin was separated and removed to obtain a liquid phase containing an acid of the anionic fluorinated emulsifier. As a result of analysis of the liquid phase, the recovery rate of the acid of the anionic fluorinated emulsifier was 90%.

Ex. 2

The treatment with an aqueous hydrochloric acid solution was carried out in the same manner as in Ex. 1 except that 6.0 g of the basic ion exchange resin having the anionic fluorinated emulsifier adsorbed thereon was charged, and the temperature was maintained at 20° C. by a constant temperature water bath. Then, a liquid phase containing the acid of the anionic fluorinated emulsifier was obtained in the same manner as in Ex. 1 except that 4.5 g of acetonitrile was charged and the temperature was maintained at 30° C. by a constant temperature water bath. As a result of analysis of the liquid phase, the recovery rate of the acid of the anionic fluorinated emulsifier was 95%.

Reference Ex. 1

Each of mixed liquids of the acid of the anionic fluorinated emulsifier and acetonitrile obtained by the method as disclosed in Ex. 1 and 2 was purified by distillation, whereupon the acid of the anionic fluorinated emulsifier with a purity of 99% or higher could be recovered.

INDUSTRIAL APPLICABILITY

The method of the present invention is applicable to recovery of an anionic fluorinated emulsifier from a basic ion exchange resin having the anionic fluorinated emulsifier adsorbed thereon.

This application is a continuation of PCT Application No. PCT/JP2014/055148 filed on Feb. 28, 2014, which is based upon and claims the benefit of priority from Japanese Patent Application No. 2013-043967 filed on Mar. 6, 2013. The contents of those applications are incorporated herein by reference in their entireties.

What is claimed is:

1. A method for recovering an anionic fluorinated emulsifier, comprising:
   contacting a strongly basic ion exchange resin having an anionic fluorinated emulsifier adsorbed thereon to an aqueous inorganic acid solution and an organic solvent comprising a nitrile group, such that the anionic fluorinated emulsifier is eluted from the strongly basic ion exchange resin and that a liquid phase comprising an acid of the anionic fluorinated emulsifier is obtained; and
   recovering an acid of the anionic fluorinated emulsifier from the liquid phase, wherein after contacting the aqueous inorganic acid solution to the strongly basic ion exchange resin, the strongly basic ion exchange resin is separated from the aqueous inorganic acid solution and recovered, and thereafter to the separated and recovered strongly basic ion exchange resin, the organic solvent is contacted, to obtain the liquid phase.

2. The method according to claim 1, wherein the aqueous inorganic acid solution is at least one member selected from the group consisting of an aqueous hydrochloric acid solution, an aqueous sulfuric acid solution, an aqueous nitric acid solution and an aqueous phosphoric acid solution.

3. The method according to claim 1, wherein the organic solvent is at least one member selected from the group consisting of acetonitrile, propionitrile, butyronitrile and isobutyronitrile.

4. The method according to claim 1, wherein the acid of the anionic fluorinated emulsifier is a fluorinated carboxylic acid.

5. The method according to claim 4, wherein the acid of the anionic fluorinated emulsifier is a $C_{5-7}$ fluorinated carboxylic acid which may have from 1 to 3 etheric oxygen atoms.

6. The method according to claim 1, wherein the concentration of the aqueous inorganic acid solution is at least 5.0 mass %.

7. The method according to claim 1, wherein the molar ratio of the acid of the anionic fluorinated emulsifier to be eluted to the aqueous inorganic acid solution is from 1/20 to 1.5/1.

8. The method according to claim 1, wherein the mass ratio of the strongly basic ion exchange resin to the aqueous inorganic acid solution is from 90/10 to 10/90.

9. The method according to claim 1, wherein the mass ratio of the strongly basic ion exchange resin to the organic solvent is from 10/90 to 70/30.

10. The method according to claim 1, wherein the molar ration of the acid of the anionic fluorinated emulsifier to be eluted to the aqueous inorganic acid solution is from 1/15 to 2/1.

11. The method according to claim 1, wherein the mass ratio of the strongly basic ion exchange resin to the aqueous inorganic acid solution is from 50/50 to 30/70.

12. The method according to claim 1, wherein the mass ratio of the strongly basic ion exchange resin to the organic solvent is from 15/85 to 60/40.

13. The method according to claim 1, wherein a recovery rate of the acid of the anionic fluorinated emulsifier is at least 90%.

* * * * *